United States Patent [19]

Kopacz

[11] 4,042,805
[45] Aug. 16, 1977

[54] STERILIZING APPARATUS

[75] Inventor: Bernard F. Kopacz, Little Falls, N.J.

[73] Assignee: Becton, Dickinson and Company, Rutherford, N.J.

[21] Appl. No.: 533,830

[22] Filed: Dec. 18, 1974

[51] Int. Cl.² ............................................. H05B 1/02
[52] U.S. Cl. .................................................. 219/492
[58] Field of Search ............ 317/142 TD, 132, 135 A, 317/135 R; 219/492, 334, 411–413, 508; 21/58; 307/113, 115, 117

[56] References Cited

U.S. PATENT DOCUMENTS

| | | | |
|---|---|---|---|
| 3,410,988 | 11/1968 | Nagel | 219/492 X |
| 3,562,490 | 2/1971 | Leach | 219/492 |
| 3,687,612 | 8/1972 | Ernst | 21/58 |
| 3,737,744 | 6/1973 | Bader | 317/135 R |

Primary Examiner—Bruce A. Reynolds
Assistant Examiner—Fred E. Bell
Attorney, Agent, or Firm—Marn & Jangarathis

[57] ABSTRACT

Sterilizing apparatus is provided in accordance with the teachings of the instant invention wherein a programmed cycle of operation is initiated and maintained unless electrical failure occurs. According to one exemplary embodiment, upon activation and cycle initiation, a door to a sterilizing chamber is locked and a control relay is latched in an enabled condition. The enabling of the control relay energizes a heater disposed in a heating relationship to the sterilizing chamber and the heat generated within said sterilizing chamber is monitored by a sensor which selectively controls the heater to maintain a selected heat within the sterilizing chamber. When a predetermined temperature within the sterilizing chamber is detected a timer is initiated for the sterilization cycle selected. Upon an expiration of the timing interval, the control relay is opened and the door to the sterilizing chamber is unlocked whereupon cycle resetting may take place upon an opening of the door to the sterilizing chamber while any interruption of the programmed sequence of events will abort the sterilizing cycle initiated.

7 Claims, 3 Drawing Figures

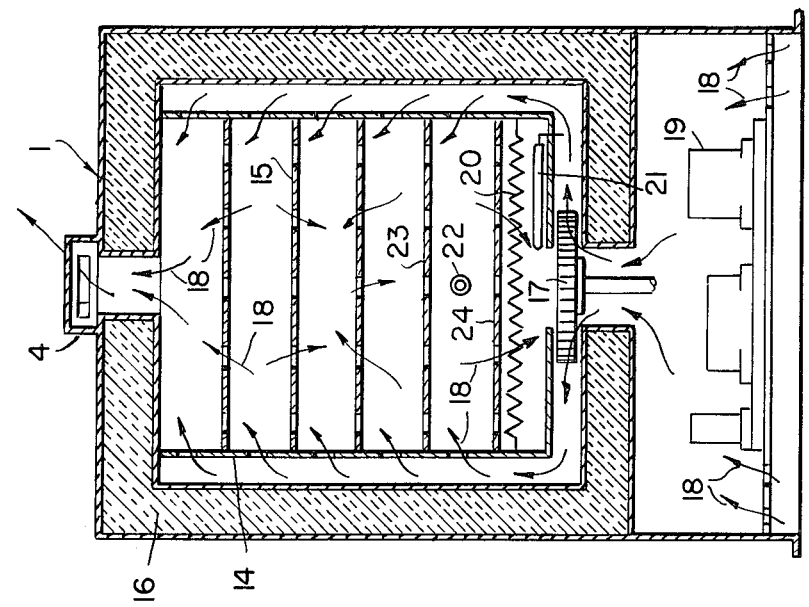
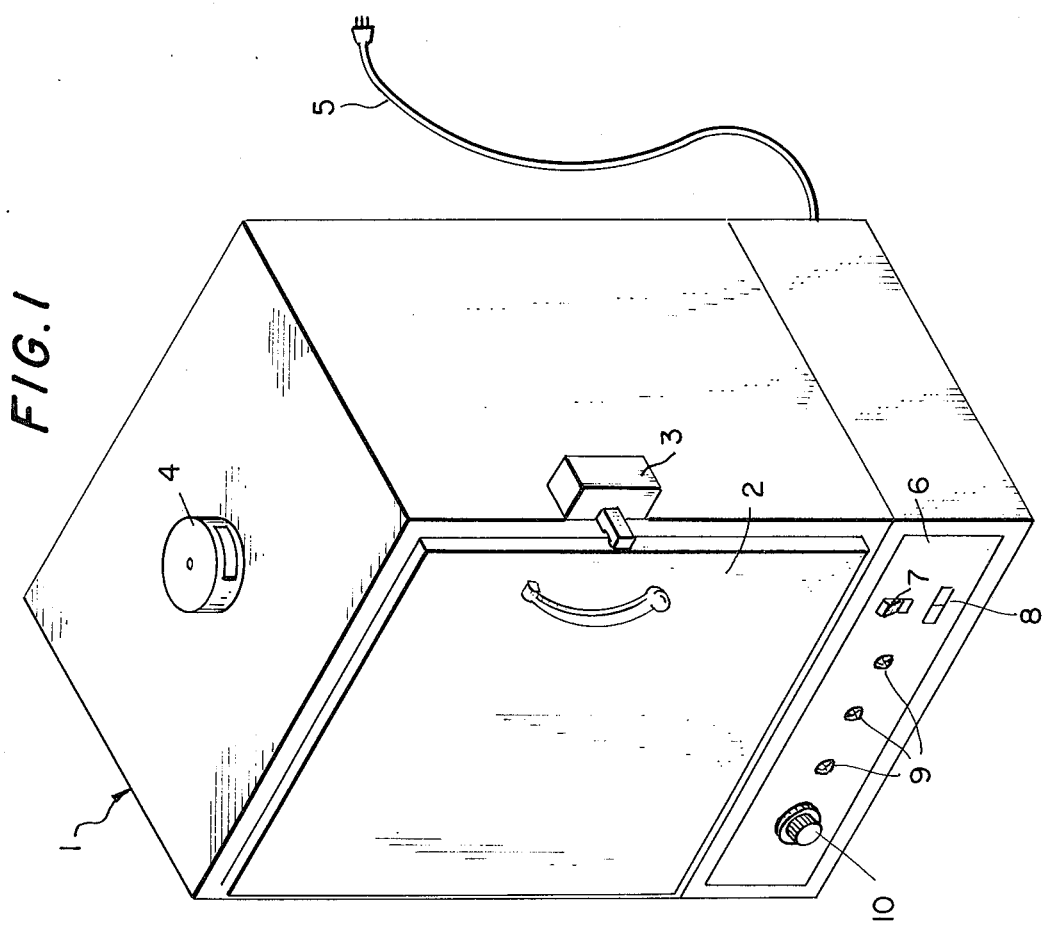

STERILIZING APPARATUS

This invention relates to apparatus for providing a constant heat within a chamber for predetermined time intervals and more particularly, to sterilizing apparatus which is both simple and safe to operate and exhibits a programmed mode of operation.

Current techniques employed in hospitals and the like for sterilizing items such as surgical implements, dressing and similar objects generally require the maintenance of such items in an environment exhibiting an elevated temperature for predetermined periods of time. The elevated temperature necessary to a sterilizing environment may be achieved through the introduction of steam to a sealed chamber or through the use of dry heat such as is obtained through the application of electrical heating techniques. Furthermore, gaseous sterilants may also be added to a sterilizing environment to quicken and otherwise advance the sterilizing operation taking place.

Steam sterilizing techniques were once preferred due to the inherently more active nature of the medium and hence the shorter completion time of a sterilization process employing these techniques. The advent of sterilizing packages employing heat actuated gaseous sterilants, such as disclosed in U.S. Pat. No. 3,494,726, which issued on Feb. 10, 1970 to Werner Barasch and is assigned to the assignee of the instant application has, however, begun to reverse this trend. This has occurred because when sterilizing packages such as are disclosed in U.S. Pat. No. 3,494,726 are employed, a sterilized item remains in a sealed, sterilized package until the same is ready to be used and hence the location of sterilizing equipment at the point of use is rendered unnecessary. Furthermore, this also obviates the need to sterilize objects just prior to use and/or the maintenance of sterilized objects in the sterilizing apparatus until such objects are required. Thus, once items are sterilized in the packages disclosed in U.S. pat. No. 3,494,726, they are maintained in a sterile condition and hence actual sterilizing operations may be conducted at remote sites and subsequently forwarded to various points of utilization. This means that large batch sterilizing operations and efficiencies are available and the speed at which a sterilizing operation is conducted is no longer of paramount concern.

Once the speed advantage of steam sterilizing techniques is removed as a significant consideration, dry heat sterilizing techniques are generally preferable from the standpoint of manufacturers and users alike. This view is taken because dry heat sterilizing apparatus may be implemented through the application of electrical heater, control and sensory equipment while the pressure chamber and pressure/temperature sensitive control devices required in a steam system may be avoided as are the deleterious effects of moisture on surgical implements. These attributes of dry heat sterilizing systems inevitably lead to manufacturing and user economies in the form of reduced cost, greater reliability and lower maintenance. Furthermore as will be appreciated by those of ordinary skill in the art, dry heat sterilizing apparatus acts to establish a substantially constant heat within a chamber for predetermined periods of time. Accordingly, such dry heat sterilizing apparatus may be employed as activation chambers for the heat activated gaseous sterilants present in sterilizing packages such as disclosed in U.S. Pat. No. 3,494,726, or to directly achieve sterilization through the establishment of elevated temperatures within a chamber for selected intervals of time.

Therefore, it is a principal object of this invention to provide dry heat sterilizing apparatus which is both simple and safe to operate and exhibits a programmed mode of operation to establish a substantially constant heat with a chamber for predetermined intervals of time. Other objects and advantages of this invention will become clear from the following detailed description of an exemplary embodiment thereof, and the novel features will be particularly pointed out in conjunction with the appended claims.

In accordance with the teachings of the instant invention, sterilizing apparatus is provided wherein, upon activation and cycle initiation, a door to a sterilizing chamber is locked and control relay means is latched in an enabled condition; the enabling of said control relay means energizes heater means disposed in a heating relationship to said sterilizng chamber and the heat generated within said sterilizing chamber is monitored by sensor means which selectively controls said heater means to maintain a selected heat within said sterilizng chamber; when a predetermined temperature within said sterilizing chamber is detected timer means is initiated for the sterilization cycle selected; upon an expiration of the timing interval, said control relay means is opened and said door to said sterilizing chamber is unblocked whereupon cycle resetting may take place upon an opening of the door to said sterilizing chamber while any interruption of the programmed sequence of events will abort the sterilizing cycle initiated. The invention will be more clearly understood by reference to the following detailed description of an exemplary embodiment thereof in conjunction with the accompanying drawings in which:

FIG. 1 is a pictorial view of an exemplary embodiment of sterilizing apparatus in accordance with the teachings of the instant invention;

FIG. 2 is a sectional view of the embodiment of the sterilizing apparatus shown in FIG. 1 and depicts the air flow which takes place therein.

Figure 3:
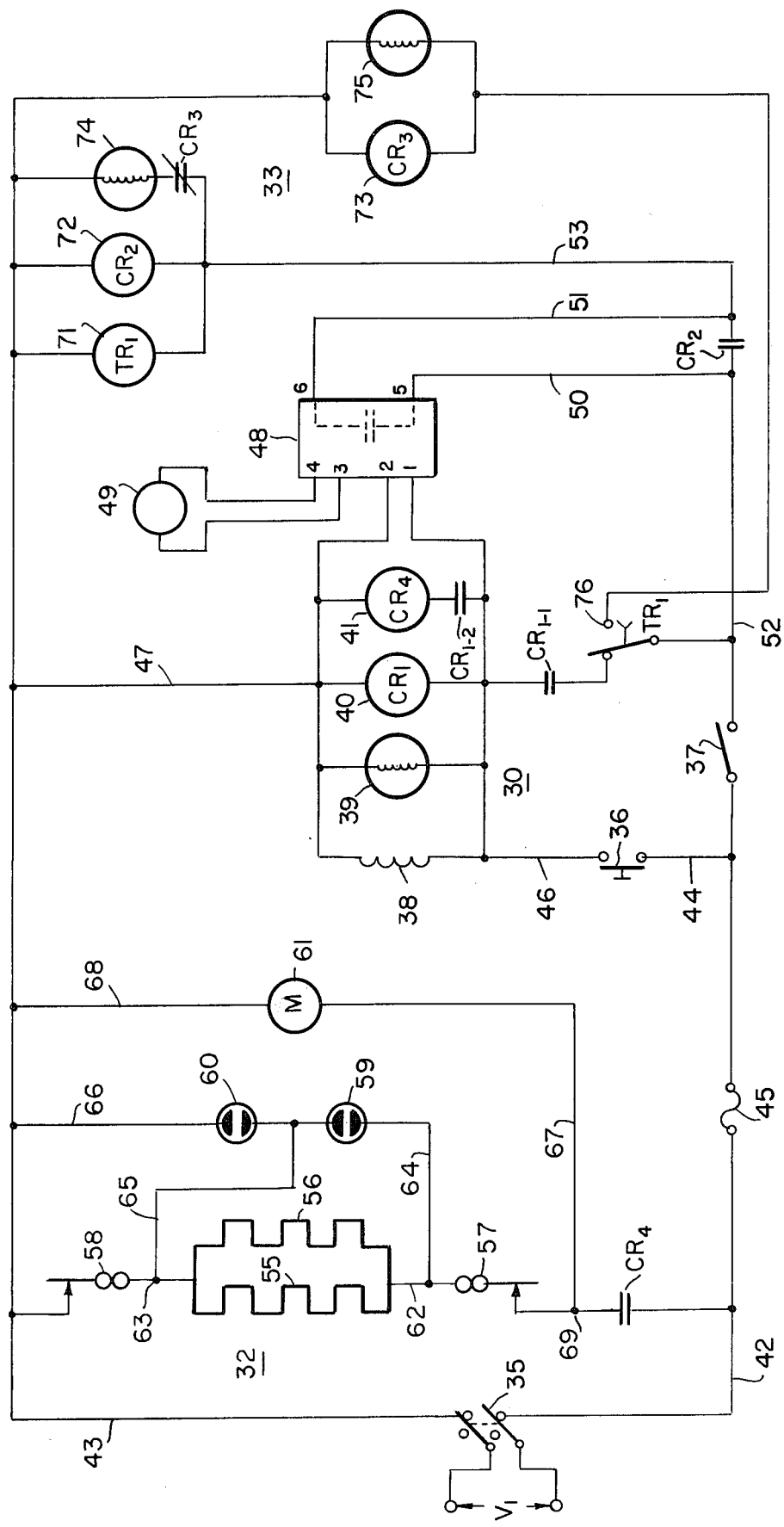
FIG. 3 is a schematic diagram illustrating exemplary heating, control and sensing circuitry for the embodiment of the invention depicted in FIG. 1.

Referring now to the drawings and more particularly, to FIG. 1 thereof, there is shown a pictorial view of an exemplary embodiment of sterilizing apparatus in accordance with the teachings of the instant invention. The exemplary embodiment of the sterilizing apparatus depicted in FIG. 1 is particularly well suited for applications wherein objects to undergo sterilization are disposed in sterilizing packages of the type disclosed in U.S. Pat. No. 3,494,726 and thus serves to activate the sterilant agents impregnated in the packages to effect sterilization through a heat activation of the gaseous sterilant. A principal function of the exemplary embodiment of the sterilizing apparatus depicted in FIG. 1 is thus to effect a constant heat over a predetermined time interval within a chamber in which sterilant packages have been disposed and to activate the sterilant agent present in said packages to cause a sterilization of the contents of each package. For this reason, as shall be seen below, the exemplary embodiment of the invention depicted in FIG. 1 is provided with a flow through forced air system which is unfettered by filtering apparatus or the like. However, it will be appreciated by those of ordinary skill in the art that for embodiments of the instant invention whose principle application is directed to sterilizing processes, not employing sterilization packages of the type disclosed above, a filtration system for the forced air system may be employed or the deletion of this air circulation may be provided without any substantial deviations from the inventive concepts set forth herein.

The exemplary embodiment of the sterilizing apparatus according to the instant invention, as illustrated in FIG. 1, comprises a main housing 1 in which a sterilization chamber is disposed, a chamber door 2, a door lock mechanism 3, a chamber air vent 4, a power cord 5 and a control panel 6. The main housing 1 may take the form of a metal frame and outer shell which serves to form a sterilizing chamber in the interior portion thereof and is insulated from the ambient environment by conventional insulating materials disposed intermediate the outer shell and the sterilizing chamber. In addition, as shall be seen more clearly in conjunction with FIG. 2, various air circulation paths are provided to establish appropriate air flow within the chamber to ensure uniform heating therein.

Access to the sterilization chamber is provided through a chamber door 2 which is mounted in such a manner that when the same is placed in a closed condition, a plunger type microswitch or the like, mounted on the main frame 1, is depressed to thereby sense the closed condition of the chamber door 2 and to provide, as shall be seen in conjunction with FIG. 3, a circuit indication as to the appropriate readiness of the sterilization apparatus for the initiation of a sterilizing operation. A door lock mechanism 3 is additionally provided, as indicated, in association with the chamber door 2 and serves, in the well known manner, to cause the locking thereof under programmed control. In this case, the door lock mechanism is actuated by the energization of a solenoid which is enabled, as shall be seen in greater detail in conjunction with FIG. 3, during the normal sequence of events which attends a sterilization operation within the instant invention. Here, however, it is sufficient to appreciate that as soon as a sterilizing operation is initiated the solenoid for the door lock mechanism 3 is actuated to thereby lock the sterilizing chamber for the duration of the sterilization program established.

The sterilizing chamber within the main housing 1 is provided with a chamber air vent 4 so that appropriate air flow within the chamber is maintained. The function of the chamber air vent 4 will be apparent during the review of the air flow within the chamber set forth in conjunction with FIG. 2. In addition, a power cord 5, which may be conventional, is provided so that the embodiment of the sterilizing apparatus depicted in FIG. 1 may be connected to a standard power source through a wall outlet or the like.

The exemplary embodiment of the sterilization apparatus according to the instant invention, as depicted in FIG. 1, is provided with a control panel 6 which serves to enable an operator to initiate a sterilizing operation in a programmed manner mandated by the instant invention and in addition thereto, to continuously apprise an operator as to the status of any sterilizing operation presently in progress. More particularly, the control panel 6 comprises a main power switch 7, heater function indicators 8, program phase indicators 9, and a start program button or the like 10. The main power switch 7 may comprise a conventional double pole, double throw toggle switch which acts to supply operating power to the exemplary embodiment of the sterilizing apparatus depicted in FIG. 1. The heater function indicators 8 may comprise conventional neon indicators which serve to apprise an operator of the appropriate or abnormal functioning of the heater. As shall be seen below, operation of the heaters may be controlled through a pair of capillary temperature controllers which serve in a primary and back-up control roles. The heater function indicators 8, thus serve to apprise the operator as to which of the controllers is in operation and hence, indicate whether or not heater operation is normal. The heater function indicators 8 may also be provided with different colored lenses to enhance the visual indicia provided to the operator.

The program phase indicators 9 may comprise conventional panel lamps or the like which, as shall be seen below, act to apprise an operator as to the present phase of a sterilizing operation in progress. The program phase indicators 9, may also be provided with different colored lenses to enhance their indicating function in specifying the state of the programmed sterilizing operation in progress. The start program button 10 may comprise a standard push button or the like which act, when depressed, to temporarily close a pair of contacts, as shall be further seen in conjunction with FIG. 3. The start program button 10 is preferably spring biased so that the contacts closed thereby will be opened as soon as the button is released so that the programmed sequence of events, as shall be described below, is carried forward under circuit control. All of the functions of the main power switch 7, the heater function indicators 8, the program phase indicators 9, and the start program button 10 will be described in greater detail in conjunction with the circuitry associated therewith and hence are not described in detail at this juncture of the instant specification.

From an operator's point of view, the operation of the exemplary embodiment of the instant invention, as illustrated in FIG. 1, is highly simplified while appropriate indicia as to the state of an operation in progress is continuously provided. Thus, with the power cord 5 disposed in an appropriate outlet, the operator need not only open the chamber door 2 and selectively position one or more sterilant packages or the like within the interior portions of the chamber in the main housing 1. Thereafter, the door 2 is closed, the main power switch 7 placed in an on condition and the start program button 10 is momentarily depressed. From this point on, a sterilization operation is conducted under program control and the operator is apprised of the state or phase of the program through the indications provided by the program phase indicators 9 while heater functioning is monitored and indicated by the heater function indicators 8. It should be noted that as soon as the start program button 10 is depressed, the door lock mechanism 3 is enabled to lock the chamber door 2 so that premature removal of objects to be sterilized is prevented until the programmed sterilization operation has been completed and should the door be forced open or power interrupted, the programmed sterilization operation is terminated and must be restarted.

Turning now to FIG. 2 there is shown a sectional view of the instant embodiment of the sterilization apparatus according to the instant invention which serves to depict the sterilization chamber defined by the main housing 1 as well as to illustrate the air flow which takes place therein. As will be seen upon an inspection of FIG. 2, the sterilization chamber formed within the main housing 1 is defined by a plurality of chamber walls 14 disposed within the main housing 1. A plurality of item separator shelves 15 are provided within the sterilization chamber and as will be appreciated by those of ordinary skill in the art, the item separator shelves 15 are preferably formed by a plurality of narrow slotted members as indicated in FIG. 2 so that a free flow of heated air may take place therebetween. The chamber walls 14 are separated from the outer shell of the main housing 1 by the thickened wall portion of the main housing indicated and insulating material 16 may be disposed between the outer shell and interior portions of the main housing 1 to serve to isolate the sterilization chamber from its ambient environment as well as to keep the outer shell of the main housing 1 cool. Additionally, an air flow path as shown is provided between the chamber walls 14 and the interior portion of the main housing 1 to enhance air circulation within and about the sterilization chamber. The top portion of the sterilization chamber is in fluid communication, as shown, with the chamber air vent 4 to achieve an appropriate exhaust function whereby a selected portion of the air within the chamber is exhausted while remaining portions thereof are recirculated to thereby maintain appropriate temperature conditions within the sterilization chamber. The bottom portion of the sterilization chamber formed is ported, as shown, and the impeller 17 of a conventional blower motor is disposed thereunder to cause a forced air circulation within and about the sterilization chamber in the manner indicated by the arrows 18.

The interior portion of the main housing 1, disposed beneath the impeller 17 is also ported, as indicated, so that fresh air may be introduced into the system. Such fresh air enters through the bottom portion of the main housing 1, as is also indicated by arrows 18, and about the program control chassis 19. Although not illustrated in FIG. 2, appropriate filtering may be provided at the air entry and exhaust ports to prevent interior portions from being contaminated should an embodiment of the instant invention be employed for sterilizing operations not associated with the sterilizing packages described above or, alternatively, a closed system may be implemented for this purpose. The impeller 17 for the forced air blower is driven by a motor, not shown herein, but described in greater detail in conjunction with FIG. 3.

The program control chassis 19 is schematically illustrated and described in conjunction with FIG. 3 and hence the program mode of operation achieved thereby will not be described at this point in the specification. The disposition of certain sensors and circuity controlled by the program control chassis 19 will, however, be described to provide a reader with a full and complete appreciation of their physical relationship within the sterilizing chamber. Thus, heater means 20 is disposed across the lower portion of the sterilizer chamber formed, so that air being recirculated within the chamber is heated to maintain an appropriate sterilization or activation temperature. The temperature of the heater means 20 is sensed by heat sensor means 21 which may here be considered to take the form of conventional capillary heat control sensor means well known to those of ordinary skill in the art. Furthermore, an air temperature sensor means 22 which may take the form of a preset thermistor circuit or thermocouple is disposed within the sterilization chamber in an appropriate position to detect the temperature of air being recirculated therein. It should be noted that the two rows of item separator shelves 23 and 24 disposed above and below the air temperature sensor means 22 are preferably left in an empty condition to enhance the function of the air temperature sensor means 22. If desired, these two rows of shelves 23 and 24 may be omitted. Preferably, however, shelf 24 would be differently configured within the sterilization chamber of the instant invention from the remaining item separator shelves 15 therein so as to form a closed heater box and thereby preclude inadvertent operator utilization of this area.

FIG. 3 illustrates a schematic diagram of an exemplary heating control and sensing circuit for the embodiment of the invention depicted in FIG. 1. The exemplary heating, control and sensing circuit illustrated in FIG. 3 comprises a start-up and air temperature sensing network indicated generally by the numeral 30, a heater control and monitoring network indicated generally by the numeral 32 and a cycle timing and indicating circuit denoted generally by the numeral 33. The start-up and air temperature sensing network generally indicated by the numeral 30 comprises main power switch 35, a start program button 36, a door closure switch 37, door lock solenoid means 38, function indicia means 39 and control relay means 40 and 41. The main power switch 35 may comprise a conventional double pole, double throw toggle switch which corresponds to the main power switch 7 illustrated on the control panel 6 shown in FIG. 1. One side of the main power switch 35 is connected, as indicated in FIG. 3 to a conventional power supply and hence this switch acts, when placed in the closed position illustrated in FIG. 3, to apply 115 volts to the exemplary heating, control and sensing circuit illustrated in FIG. 3. Thus, whenever the main power switch 35 is closed, 115 volts are placed across conductors 42 and 43 and it will be appreciated by those of ordinary skill in the art that the main power switch is closed prior to the initiation of any sterilization cycle.

The start program button 36 may comprise a conventional single pole push button or the like whch acts in the well known manner to make a pair of contacts when depressed and thereafter opens when the button per se is released. The start program button 36 corresponds to the start program button 10 illustrated on the control panel 6 in FIG. 1 and it will be appreciated by those of orindary skill in the art that the function of the start program button is to initiate a sterilizing cycle once items to be sterilized have been loaded into the sterilization chamber, the door to the chamber has been closed and the main power switch 35 has been placed in an on condition. Further, it should be noted, as shall be rendered apparent below that all three of these functions must have been completed prior to the depression of the start program button for a program cycle in a sterilizing operation to be initiated thereby and the failure to complete any one of these steps will preclude the start up of a sterilization operation upon the depression of the start program button 36. One pole of the start program button 36 is connected through conductor 44, a conventional fuse 45, and conductor 42 to one pole of the main power switch 35 while the second pole of the start program button 36 is connected through conductors 46 and 47, the parallel circuit formed by the door lock solenoid 38, the function indicator means 39 and the control relays 40 and 41 to the conductor 43 and hence to the second side of the main power switch 35. Thus, it will be appreciated by those of ordinary skill in the art that the simple depression of the start program button 36 will cause operating potential to be applied across each of the four elements in the parallel circuit formed by the door lock solenoid 38, the function indicator means 39, and the control relays 40 and 41; however, as the closure of the contacts upon a depression of the start program button 36 is momentary, the application of power to the parallel circuit formed by these elements due to the depression of the start program button 36 is temporary in nature.

Additionally, the start program button 36 is connected in parallel with the door closure switch 37, a pair of relay contacts $TR_1$ normally in the condition shown and a pair of contacts $CR_{1-1}$ associated with the control relay 40. The door closure switch 37, as briefly mentioned above, may comprise a plunger type switch which is placed in a closed condition upon the closure of the door to the sterilizing chamber due to a closure of a microswitch when the plunger associated therewith is depressed. The door closure switch 37 may conveniently be mounted in the frame associated with the door to the sterilizing chamber so that the same is depressed upon the closure of the door. The pair of contacts annotated $CR_{1-1}$ are associated with the control relay 40 and here function, as will be appreciated by those of ordinary skill in the art, to latch the parallel circuit formed by the door lock solenoid 38, the function indicator means 39 and the control relays 40 and 41 in an energized condition provided that the door to the sterilizing chamber is closed and the start program button has been depressed. More particularly, it was seen that when the main power switch is in an on condition and the start program button 36 is depressed, power will be applied across the parallel circuit formed by the door lock solenoid 38, the function indicator means 39 and the control relays 40 and 41. This will temporarily apply power across the parallel circuit so that at least the door lock solenoid 38, the function indicator means 39 and the control relay 40 will be temporarily placed in an energized condition. Therefore, if the door to the sterilization chamber is in a closed condition, door closure switch 37 will be closed and hence, the temporary energization of control relay 40 will cause the contacts annotated $CR_{1-1}$ to be closed to thereby effectively latch the parallel circuit across the power supply due to the normal condition of timer relay contacts $TR_1$ illustrated in FIG. 3. However, should the door to the sterilization chamber not be closed, the parallel circuit formed will not be latched and power will not be maintained thereto when the start program button 36 is released.

The door lock solenoid 38 may comprise a conventional solenoid which acts in the well known manner, when energized, to activate the door lock mechanism 3 illustrated in FIG. 1. Therefore, it will be appreciated by those of ordinary skill in the art that upon appropriate initiation of a sterilizing cycle of operation, upon a depression of the start program button 36, the door to the sterilizing chamber will be placed in a locked condition due to the energization of the door lock solenoid 38 and maintained in this condition until the cycle terminates and the contacts $TR_1$ and $CR_{1-1}$ are opened. Similarly, the application of power and the maintenance thereof across the parallel circuit will cause the energization of the function indicator means 39. The function indicator means 39 may comprise a conventional pilot light with an appropriate colored lens to indicate to an operator that a sterilizing cycle has been initiated. The function indicator means 39 would normally comprise one of the program phase indicators 9 illustrated on the control panel 6 in FIG. 1 and it will be appreciated that this indicator, once illuminated, is retained in this condition until power is removed from the parallel circuit by an opening of the contacts $TR_1$ and $CR_{1-1}$ at the completion of the sterilization cycle. Although not illustrated in FIG. 3, an audible indicator which may be timed, may also be connected in parallel across the function indicator means 39 to provide an audible function signal. Should this form of advisory be employed, a timing of the duration would be a preferable mode of implementation.

The control relay 40 may comprise a conventional double pole, double throw plug in relay of the type well known to those of ordinary skill in the art, or alternative apparatus for achieving a similar function may be substituted therefor. The control relay 40 has two pairs of normally open contacts which are closed upon configuration thereof. The first pair of contacts annotated $CR_{1-1}$ have been previously described and serve to latch this relay in a closed condition as aforesaid. The second pair of contacts associated with the control relay 40 are annotated $CR_{1-2}$ and are connected in series with the second control relay 41. This pair of contacts is also in a normally opened condition and is closed upon the energization of the control relay 40 which is identified as $CR_1$. Thus, it will be appreciated by those of ordinary skill in the art that when the start program button 36 is depressed and the door closure switch 37 is appropriately closed, control relay 40 is actuated to cause the parallel network formed by the door lock solenoid 38, the function indicator means 39 and control relays 40 and 41 to be latched across the power supply due to the closing of contacts $CR_{1-1}$ while the closure of the second pair of contacts $CR_{1-2}$ of control relay 40 causes control relay 41 to be actuated.

The parallel network formed by the door lock solenoid 38, the function indicia means 39, and the control relays 40 and 41 is additionally connected in parallel, as indicated in FIG. 3, to contacts annotated 1 and 2 of a temperature controller 48. The temperature controller 48 may comprise any of the well-known forms of this conventional class of devices and acts, when energized, to sense the ambient temperature surrounding the probe portion thereof and to close a pair of contacts whenever such temperature exceeds a selected value. A thermistor probe as indicated by the circle 49, is connected to terminals 3 and 4 of the temperature controller means 48 and the temperature selected for actuation purposes is selectable within a range of 0° – 400° F. although other suitable ranges are available for sterilization apparatus according to the instant invention The actual placement of the thermistor probe 49 within the sterilization chamber is illustrated in FIG. 2 in the position of the air temperature sensor means 22. As the principal application of the instant embodiment of the sterilizing apparatus according to the subject invention is to activate the sterilant gas within sterilizing packages, the activation temperature for the temperature controller means 48 would normally be preset at approximately 60° C; however, the actuation temperature of the temperature controller means 48 is readily variable and should it be desired to provide an embodiment of this invention wherein temperature setting controls are available to an operator, the adjustment means for the temperature controller means 48 may be disposed on the control panel 6 shown in FIG. 1 with appropriate graduations for operator selection. Furthermore, it will be seen hereinafter that temperature sensor means are also provided on the heater. Therefore, should it be desired to provide readily available operator selectivity for the temperature control means 48, similar controls for the heat sensors of the heater may also be provided at the control panel and appropriately ganged, if desired, to the heat setting means for the temperature controller means 48.

When power is applied across terminals 1 and 2 of the temperature controller means 48 and the temperature sensed by the thermistor probe 49 is above a selected setting, the temperature controller means 48 acts in the well known manner to close a pair of contacts disposed between terminals 5 and 6 so that a short circuit condition resides therebetween. This has been indicated in FIG. 3 by the dashed contacts illustrated within the temperature controller means 48 as well as by the dashed connections thereto. Thus, it will be appreciated that once the door switch 37 is closed and the start program button 36 has been depressed, the application of power to the parallel circuit formed by the door lock solenoid 38, the function indicia means 39, and the control relays 40 and 41 will cause the door to be locked, a program in progress indication to be displayed and the closure of relay 40 which causes this relay to be latched in circuit to maintain power across the parallel network and to cause the enabling of the control relay 41 through the pair of contacts annotated $CR_{1-2}$. In addition, operating power is applied from the parallel circuit to terminals 1 and 2 of the temperature controller means 48 so that the same may begin a sensing of the temperature within the sterilizing chamber. The terminals 5 and 6 are connected through conductors 50 and 51 across a pair of relay contacts annotated $CR_2$ which are interposed between the conductors 52 and 53. From the operation of the temperature controller means 48 described above, it will be appreciated by those of ordinary skill in the art, that once a selected temperature has been detected by the thermistor probe 49, a short will be established across terminals 5 and 6 so that the relay contacts $CR_2$ will be shunted. This function of the temperature controller means 48, as will be seen below, acts to initiate the operation of the cycle timing and indicating circuit generally indicated by the numeral 33, once appropriate temperature within the sterilizing chamber has been indicated so that the next step in the program sequence associated with a sterilizing operation is initiated.

The heater control and monitoring network 32 comprises heater means 55 and 56, primary and back-up heat sensor means 57 and 58, sensor function indicator means 59 and 60 and blower motor means 61. The heater control and monitoring network 32 is connected intermediate conductors 42 and 43 and hence, across the power supply through a pair of relay contacts annotated $CR_4$. These contacts, as will be appreciated by those of ordinary skill in the art, are closed upon the enabling and subsequent latching of the control relay 40 and more particularly upon an enabling of control relay 41. Therefore, it will be appreciated by those of ordinary skill in the art that the heater control and monitoring network 32 is not energized until such time as a program sterilizing operation is initiated by the depression of the start program button 36 and is maintained through a latching of the control relay 40. The heater means 55 and 56 may take the conventional form of electrical heating coils well-known to those of ordinary skill in the art. Although a pair of such coils have been indicated in FIG. 3, it will be readily appreciated that a greater or lesser number of coils may be employed for the heater means 55 and 56 depending upon the normal temperature range of operation for the embodiment of sterilizing apparatus being designed and the heating efficiencies desired. The lower terminal portions of the heater means 55 and 56 are commonly connected, as indicated in FIG. 3, to a junction point 62 while the upper terminal portions of the heater means 55 and 56 are commonly connected to junction point 63.

The junction point 62 is connected to one terminal of the primary heat sensor means 57 and a conductor 64 while the junction point 63 is commonly connected to one terminal of the back-up heat sensor means 58 and a conductor 65. The primary and back-up heat sensor means 57 and 58 may take the conventional form of capillary controllers such as are available from the Fenwal Corporation or the Honeywell Corporation and effectively act to maintain the heater means 55 and 56 across the power supply until a selected temperature is exhibited thereby and thereafter to open the contacts thereof until the temperature of the heater means 55 and 56 is reduced through the air flow taking place to below the selected temperature. Preferably, the opening and closure of the capillary controllers employed for the primary and back-up heat sensor means 57 and 58 exhibits a predetermined hysteresis to avoid undue opening and closure of the contacts of the capillary controllers. Thus, preferably, the primary and back-up heat sensor means 57 and 58 would be designed to open at a first temperature and close at a second temperature which is a few degrees below that selected for opening. The condition of the primary and back-up heat sensor means 57 and 58 is normally closed and the temperature at which they will open is selectable within a wide range. For the exemplary case of sterilizing apparatus primarily adapted for use in conjunction with heat actuated gas sterilants encased within sterilizing packages, the primary heat sensor means 57 would be set at the same temperature selected for activation of the temperature controller means 48 and hence the desired activation temperature within the sterilizing chamber. As the heat sensor means 57 and 58 are employed in a primary and back-up mode to ensure that heaters will not be left in an on condition due to an inadvertent failure, the temperature selection controls on both the primary and back-up heat sensor means 57 and 58 are preferably ganged so that the temperature for the activation or opening of the back-up heat sensor means 58 is automatically established a few degrees, for example, 5° C., above that established for the primary heat sensor means 57. During normal operation, the primary heat sensor means 57 will be opening and closing as a desired temperature is reached and then lost by the heater means 55 and 56 during a sterilizing operation. However, should the primary heat sensor means 57 fail in a closed condition, the opening and closing function will be taken over by the back-up heat sensor means 58 prevent objects undergoing sterilization from being damaged from excessive heat. Thus it will be appreciated that once a program cycle of operation is initiated and the latching of control relay 40 causes the enabling of control relay 41, contact $CR_4$ will be closed whereupon the operation of the heater means 55 and 56 will be automatically controlled in relation to a selected temperature by the operation of the primary and back-up heat sensor means 57 and 58.

The operation of the primary and backup heat sensor means 57 and 58 is monitored by the sensor function indicator means 59 and 60. The sensor function indicator means 59 and 60 may take the form of conventional neon tubes as indicated and serve to provide an indication as to the normal operation of the primary heat sensor means 57 or the abnormal operation of the back-up heat sensor means 58. More particularly, the sensor function indicator means 59 is associated with the primary heat sensor means 57 and acts to provide a visual indication whenever power is being applied to the heater means 55 and 56 due to the closed condition of both the primary and back-up heat sensor means 57 and 58 while being in a non-energized condition whenever the primary heat sensor means 57 is opened. In reverse manner, the sensor function indicator means 60 is associated with the back-up heat sensor means 58 and acts to provide a visual indication only under such conditions as when the primary heat sensor means 57 is in a closed condition while the back-up heat sensor means 58 is opened; it being recalled that this condition should only persist under such conditions when the primary heat sensor means 57 has failed in a closed condition and heater operation is being controlled by the back-up heat sensor means 58 whereupon back-up control has thus been lost and servicing should occur upon the completion of the sterilizing program presently in process. Preferably, the sensor function indicator means 59 and 60 are provided with different colored lens caps and are positioned on the control panel 6 illustrated in FIG. 1 in the position of the heater functions indicators 8. If desired, audible alarms may be connected in parallel with each of the sensor function indicator means 59 and 60 and it may well be desired to complement at least the operation of sensor function indicator means 60 with an audible alarm so that the operator will not continue to operate the sterilizing apparatus according to the instant invention after the primary heat sensor means 57 has failed in a closed condition.

As neon tubes such as may be employed for the sensor function indicator means 59 and 60 are voltage responsive devices, the inverse sensing operation associated with the sensor function indicator means 59 and 60 will be apparent to those of ordinary skill in the art. Thus, an inspection of FIG. 3 will indicate that the sensor function indicator means 59 associated with the primary heat sensor means 57 is connected across the heater means 55 and 56 through conductors 64 and 65 to the junction points 62 and 63. Therefore, sensor function indicator means 59 will be illuminated only during such times as a voltage drop occurs across the heater means 55 and this will only occur when both the primary and back-up heat sensor means 57 and 58 are in a closed condition. However, any time the primary heat sensor means 57 in an opened condition, junction points 62 and 63 will be at the same potential and hence no voltage drop will be available to illuminate the sensor function indicator means 59 associated with the primary heat sensor means 57. Accordingly, during normal operation where the energization of the heater means 55 and 56 is being controlled by the primary heat sensor means 57, the sensor function indicator means 59 will be illuminated whenever energy is being applied to the heater means 55 and 56 due to the closed condition of the primary heat sensor means 57 while this indicator will be in a non-illuminated condition whenever the primary heat sensor means 57 is opened. Conversely, sensor function indicator means 60 is connected through conductors 56 and 66 across the back-up heat sensor means 58 and hence will only be illuminated when the primary heat sensor means 57 is in a closed condition while the back-up heat sensor means 58 is in an opened condition to thereby supply a potential drop between the conductor 43 and junction point 63. However, when the back-up heat sensor means is in a closed condition, junction point 63 and conductor 43 will be at the same potential to thereby provide a zero (0) potential across the sensor function indicator means 60. Thus it will be appreciated that persistent flashing of sensor function indicator means 60 during a programmed cycle of operation is indicative that the primary heat sensor means 57 has failed in a closed condition and that the temperature control of the heater means 55 and 56 is being controlled by the back-up heat sensor means 58 so that mandatory servicing to restore the back-up safety feature is appropriate.

The motor means 61 is connected through conductors 67 and 68 between the conductor 43 and a junction point 69 intermediate the relay contacts $CR_4$ and the primary heat sensor means 57. The motor means 61 may take any conventional form of blower motor means and is here employed to drive the impeller 17 illustrated in FIG. 2 to provide appropriate air circulation, as aforesaid, within the sterilization chamber. As will be appreciated by those of ordinary skill in the art from the circuit set forth, the motor means 61 is thus energized any time the relay contacts $CR_4$ are closed and thus continues to cause appropriate air circulation within the sterilization chamber despite momentary disabling or enabling of the heater means 55 and 56.

The cycle timing and indicating circuit 33 comprises timer relay means 71, control relay means 72 and 73 and function indicator means 74 and 75. The timer relay means 71, the control relay means 72 and the function indicator means 74 are disposed in a parallel circuit which is arranged to be placed across the potential on conductors 43 and 52 upon a detection by the thermistor means 49 of an appropriate temperature within the sterilization chamber and the consequent short established between terminals 5 and 6 of the temperature controller means 48. The timer relay means 71 may comprise a conventional automatic timing clock, which, once energized by the appropriate application of potential thereto, initiates an appropriate timing cycle and upon the termination of such timing cycle acts to shift a pair of contacts annotated $TR_1$ in FIG. 3. The contacts associated with the timer relay means 71 are annotated $TR_1$ in FIG. 3 and it should be appreciated that the contacts are normally disposed in the position illustrated to complete a path from conductor 52 to conductor 47 and will only be displaced to terminal 76 upon an enabling of the timer relay means 71 and the subsequent timing out of the timing cycle set thereby. The timer relay means 71 may comprise a portion of a conventional 0 to 10 hour automatic timing clock whose timing interval, in the instant embodiment of the present invention is preset for approximately a 6 hour cycle. As was the case for the temperature controller means 48 and the primary and back-up heat sensor means 57 and 58, operator settings are not made available at the control panel 6, as shown in FIG. 1; however, the same could be made available should this feature be deemed desireable. It should be noted that for sterilizing cycles associated with sterilizing packages, if the activation temperature established for the temperature controller 48 is 60° C., a 6 hour timing cycle is appropriate while if a 70° C. setting is utilized, sterilization may be satisfactorily achieved within a 4 hour cycle due to the more rapid release of the gaseous sterilant at elevated temperatures. Thus, should it be desireable to make interval timing and temperature activation controls available for operator setting at the control panel 6, a ganged feature between these controls may be employed to enforce an appropriate time-temperature relationship. Accordingly, once an appropriate temperature is detected in the sterilizing chamber, the relay contacts $CR_2$ are bridged across by the action of the temperature controller means 48 to thereby initiate cycle timing by the time relay means 71.

When power is applied across the timer relay means 71 due to the establishment of a short circuit across conductors 50 and 51 by the temperature controller means 48, operating potential is also applied across relay means 72. The control relay means 72 may comprise a conventional double pole, double throw, plug in relay of the type described in conjunction with control relay 40 and here acts, when enabled, to close a pair of normally opened contacts $CR_2$. This action, effectively latches the parallel circuit formed by the timer relay means 71, the control relay means 72, and the function indicator means 74 across operating potential regardless of whether or not temperature within the sterilizing chamber, as sensed by the thermistor 49, drops to cause an open circuit to occur between conductors 50 and 51. Should this result not be viewed as desireable, as would clearly be the case in dry heat sterilizing apparatus in which plastic sterilizing packages not employing gaseous sterilants are used, the pair of relay contacts annotated $CR_2$ could be omitted together with the control relay means 72. However, as shall be more fully appreciated below, a secondary pair of relay contacts associated with control relay means 73 should then be employed to bridge between conductor 52 and terminal 76 to maintain power to the function indicator means 75 under such conditions where the timing relay has timed out and an end of cycle condition is being indicated since, under these conditions, power would be removed from timer relay means 71 causing contacts $TR_1$ to shift. Additionally, upon the actuation of the temperature controller means 48 and/or the closure of control relay means 72, operating potential is applied across the function indicator means 74 through a normally closed pair of relay contacts annotated $CR_3$. The function indicator means 74 may take the same form of pilot light configuration described in association with function indicator means 39; however, it is preferably provided with a different colored lens. The function indicator means 74 is disposed on the control panel 6 illustrated in FIG. 1 and thus when the same is illuminated, appropriately apprises an operator that an appropriate temperature within the sterilizing chamber has been reached and the timing cycle for the programmed sterilization sequence has been initiated. As was the case for the pilot lamp 39, an audible indicator may be connected in parallel with the function indicator means 74 to provide an operator with an audible indication of cycle progress.

Upon a tming out of the timing relay means 71, the contacts annotated $TR_1$ associated therewith are shifted from the position shown so that a connection is established between conductor 52 and terminal 76. This causes an enabling of the control relay means 73 and the function indicator means 75. When the control relay 73 is actuated, relay contacts $CR_3$ associated therewith are placed in an open condition to thereby extinguish the function indicator means 74 which indicates, as aforesaid, that a timed sterilizing sequence is still in progress. However, the function indicator means 75 is illuminated to indicate that the sterilization operation has been completed and to thereby otherwise apprise an operator that the contents of the sterilization chamber may be removed. It will also be noted that upon a shifting of the contacts $TR_1$ to terminal 76, the parallel circuit formed by the door lock solenoid 38, the function indicator means 39, and the control relay 40 and 41 is de-energized whereupon the door to the sterilization chamber is unlocked, the heater is disabled by the control relay 41 and the latching circuit associated with control relay 40 is disabled. The function indicator means 75 may take the same form of pilot lamp described in association with function indicator means 74 and is also provided with a different colored lens and disposed on the control panel 6 for convenient indication to an operator.

In operation of the exemplary embodiment of the sterilizing apparatus in accordance with the teachings of the instant invention, an operator would normally load objects to be sterilized, preferably disposed in sterilizing packages of the type containing a heat activated gaseous sterilant, as aforesaid, on the item separator shelves 15 within the sterilizing chamber. Thereafter, the main power switch 35, as shown in FIG. 3, would be placed in an ON or closed condition and the start program button 36 depressed. When the main power switch 35 is closed, appropriate potential $V_1$ is placed across conductors 42 and 43 as shown in FIG. 3. Therefore, upon a depression of the start program button 36, this potential is applied across the parallel circuit formed by the door lock solenoid 38, the function indicia means 39, control relays 40 and 41 as well as to input terminals 1 and 2 of the temperature controller means 48. It it is further assumed that the foregoing actions were preceded by the appropriate closure of the door to the sterilizing chamber, it will be appreciated that the door closure switch 37 is in a closed position due to the plunger actuated microswitch associated therewith. Accordingly, the momentary application of voltage across the parallel circuit due to the depression of the start program button 36 will cause the door lock solenoid 38 to be energized whereupon the door to the sterilizing chamber is locked in response to the action of the door lock mechanism 3 shown in FIG. 1, the function indicator means 39 will be illuminated to indicate a sterilizing program has been initiated and the control relay 40 will be enabled.

Upon the enabling of the control relay 40, the contacts $CR_{1-1}$ and $CR_{1-2}$ are closed. This latches the control relay 40 and the parallel circuit into an energized condition due to the normally closed conditions of the contacts $TR_1$ illustrated in FIG. 3 so that the parallel circuit remains energized despite the release of the start program button 36. When the relay contacts $CR_{12}$ are closed, the control relay 41 is also enabled. Upon the enabling of control relay 41, relay contacts $CR_4$ associated therewith are closed whereupon the potential across conductors 43 and 44 is applied to the heater control and monitoring network shown generally at 32. Additionally, as the temperature controller means 48 is enabled by the application of power across input terminals 1 and 2 thereof, the thermistor probe 49 begins a sensing of the temperature within the sterilizing chamber.

When the relay contacts $CR_4$ are closed, the primary and back-up heat sensor means 57 and 58 may be assumed to be in the closed condition shown so that the application of potential across the heater control and monitoring network 32 results in an energization of the heater means 55 and 56 and the motor means 61 whereupon the impeller 17 shown in FIG. 2 initiates a forced air flow within the sterilizing chamber. Additionally, the voltage drop present across the heater means 55 and 56 will cause the sensor function indicator means 59 to be illuminated indicating that normal heater operation being controlled under the influence of the primary heat sensor means 57 is in progress. Under these conditions, the heater means 55 and 56 will rapidly approach a temperature of approximately 40° C. and the heat therefrom will rapidly be communicated throughout the sterilizing chamber due to the forced air flow initiated by the energization of the motor means 61. Once this temperature is reached, the temperature of the heaters will gradually increase to the selected activation temperature for the gaseous sterilant which here may be assumed to be approximately 60° C., it being noted that a higher selected temperature for activation apparently results in a more rapid release of the gaseous sterilant.

When the desired temperature for the activation of the gaseous sterilant is reached by the heater means 55 and 56, assuming normal functioning of the primary heat sensor means 57, an open condition of the contacts therein will result to cause a temporary disabling of the heater means 55 and 56 and a consequent extinguishing of the neon tube which serves in the role of the sensor function indicator means 59. However, when the heater means 55 and 56 cool below the selected threshold temperature, the primary heat sensor means 57 will again close to again enable the heater means 55 and 56 and cause the sensor function indicator means 59 to be illuminated. Thus, in this manner, assuming the normal operation of the primary heat sensor means 57, the heater means 55 and 56, upon reaching a desired temperature, will be cycled on and off to maintain a predetermined temperature under the control of the primary heat sensor means 57 and each time operating power is applied across the heater means 55 and 56, the sensor function indicator means 59 will be illuminated while the motor means 61 is maintained in an energized condition throughout the sterilizing cycle.

If it is assumed however, that for some reason the primary heat sensor means 57 fails in a closed condition, the control for the periodic enabling and disabling of the heater means 55 and 56 shifts to the back-up heat sensor means 58. The back-up heat sensor means 58, it will be recalled, has its temperature setting ganged to the temperature setting of the primary heat sensor means 57 in such manner that the selected actuation temperature thereof is established approximately 5° C. above that selected for the primary heat sensor means 57. Therefore, if the primary heat sensor means 57 fails in a closed condition, when the temperature associated with the heater means 55 and 56 reaches a temperature exceeding 5° above the setting established for the primary heat sensor means 57, the back-up heat sensor means 58 will be placed in an opened condition. When the contacts on the back-up heat sensor means 58 are opened, the heater means 55 and 56 will be disabled and the neon tube serving in the role of the sensor function indicator means 60 will be illuminated to apprise the operator that the back-up control system for the heaters have been brought to bear and hence maintenance on the system is required. However, regardless of whether the periodic actuation of the heater means 55 and 56 is controlled by the primary or back-up heat sensor means 57 or 58, once the heater means 55 and 56 reach a temperature proximate to that selected, the heater means 55 and 56 will be gated on and off to maintain this temperature within the environment of the sterilizing chamber and due to the provision of primary and back-up heat sensor means 57 and 58 so that there is little practical possibility that the heater means 55 and 56 will be maintained in an energized condition for periods which might cause damage to articles being sterilized.

When the temperature within the sterilizing chamber, as sensed by the thermistor probe 49, reaches the selected temperature set at the heat controller means 48, the heat controller means 48 will effect a closure of the contacts therein residing between terminals 5 and 6. This effectively connects conductors 52 and 53 together through conductors 50 and 51 to effect the application of power to the parallel circuit formed by the timer relay means 71, the control relay means 72, and the function indicator means 74. When power is applied to this parallel circuit, the timing relay means 71 will initiate its automatic timing cycle which may here be viewed as comprising approximately a 6 hour interval if the activation temperature selected is 60° C. and a 4 hour interval should a 70° activation temperature be selected. In addition, the control relay 72 is enabled and the function indicator means 74 is illuminated due to the normally closed condition of relay contacts $CR_3$, as indicated in FIG. 3. When the control relay 72 is enabled, contacts $CR_2$ are closed to thereby latch enabling potential to this relay and hence to the parallel circuit formed by the timer relay means 71, control relay means 72, and function indicator means 74. Thus, through the action of the function indicator means 74, the operator is apprised that appropriate sterilization temperatures have been reached within the sterilizing chamber and that a timed sterilizing operation has been initiated under program control. Furthermore, the operation of the control relay means 72 effectively latches the parallel circuit formed by the timer relay means 71, the control relay means 72 and the function indicator means 74 to continue the energization of this circuit, regardless of subsequent heat variations within the sterilizing chamber, until such time as the timer relay 71 times out or an interruption in electrical potential effects a resetting of the circuit.

It should be noted that this particular mode of operation has been here selected to complement the programmed mode of operation of a timer which is automatically reset each time the same is de-energized together with the independent control of the heaters accomplished through the primary and back-up heat sensor means 57 and 58. However, should it be desired to employ a continuous monitoring of the temperature within the chamber through the operation of the thermistor probe 49 and the temperature controller means 48, the electrical latching of the timer relay $TR_1$ and the control relay $CR_2$ through relay contacts $CR_2$ could be deleted. Under these conditions, the choice of an automatic timing circuit and timer relay 71 therefor may be modified so that automatic resetting would not take place should the contacts associated with terminals 5 and 6 of the temperature controller means 48 open due to a temporary drop in temperature within the chamber. Alternatively, an automatic resetting for the entire sterilizing interval might be desireable. Additionally, under these conditions, as shall be apparent to those of ordinary skill in the art from the circuit operation described hereinafter, a second set of bridge contacts associated with the control relay 73 would be connected intermediate terminal 76 and the armature portion of relay contacts TR₁ to ensure that a sterilizing interval completed signal is maintained upon the timing out of the timing relay 71. Accordingly, in the instant exemplary circuit, once the timed sterilizing interval is initiated upon the closure of switch contacts maintained between terminals 5 and 6 in the temperature controller means 48, the energization of the control relay 72 effects a latching of power to the timer relay 71 so that the programmed timing interval will continue unless a momentary interruption in the main power source occurs to abort the entire cycle and to thus require a re-initiation of the programmed sequence of events initiated by the depression of PB1. However, as will now be apparent to those of ordinary skill in the art, a cycle aborting sequence may be initiated by removing the control relay 72 together with latching contacts CR₂ while an automatic timer employing resetting upon a removal of power may be retained, a timer whose operation is such as to cause a mere pause in the timing sequence may alternatively be substituted therefor, or more sophisticated timing circuitry may be employed whose operation is such that pauses are acceptable to the operation thereof so long as such pauses persist for only a predetermined interval set under the control of a secondary timer and any pause exceeding this interval will cause the operation of the automatic timer to be reset.

Upon the completion of the sterilizing interval established by the automatic timer, the timer relay 71 will shift to a secondary condition whereupon contacts TR₁ close to terminal 76. When the contacts TR₁ of the timing relay TR₁ shift to the terminal 76, operating power is applied across the parallel circuit formed by the control relay means 73 and the function indicator means 76. This action, as will be readily appreciated by those of ordinary skill in the art, will cause the control relay means 73 to be enabled and the function indicator means 75 to be illuminated so that the operator is apprised that the programmed sterilizing sequence has been completed. In addition, the shifting of the timer relay contacts TR₁ will cause operating power to be removed from the parallel circuit formed by the door lock solenoid 38, the function indicator means 39, and control relay 40 and 41. When the control relay means 73 is enabled, the normally closed contacts CR₃ thereof will open to extinguish the timed program sterilization sequence underway indication and provided by the function indicator means 74. In addition, the shifting of contacts TR₁ to terminal 76 will cause the door lock solenoid 38 to release, the programmed cycle of operation initiated indication provided by the function indicator means 39 to be extinguished and the control relay means 40 to be de-energized to thereby open contacts CR₁₋₂ and hence de-energize the control relay 41. This in turn causes contacts CR₄ to open and thereby de-energize the heater means 55 and 56. Thus, upon completion of the timing interval established by the control relay 71, the automatic sterilizing apparatus according to the instant invention is placed in a de-energized, stand-by condition, where no new cycle of operation may be initiated until a further re-setting of the apparatus occurs since both the timing relay 71 and the control relay means 72 are maintained in an energized condition as is the control relay means 73 and the function indicator means 75. Resetting, as will be apparent to those of ordinary skill in the art, occurs, only at such time as the operator actually opens the door to the automatic sterilizing chamber to remove items which have been sterilized during the previous operation. When the operator opens the door to the sterilizing chamber, under these conditions, the door closure switch 37 opens up to thereby disable the application of power to both the parallel circuits formed by the timer relay 71 and the control relay means 72 as well as the parallel circuit formed by the control relay 73 and the function indicator means 75. At this time, the timer relay 71 automatically resets while the control relay means 72 and 73 are opened to effect a complete resetting of the automatic sterilizing apparatus according to the instant invention.

Therefore, it will be appreciated by those of ordinary skill in the art that the dry heat sterilizing apparatus according to the instant invention is both simple and safe in operation and exhibits a programmed mode of operation to establish a substantially constant heat within a chamber for predetermined intervals of time. Although the instant invention has been disclosed in accordance with a preferred embodiment, many variations and alterations in the specific circuits disclosed will be apparent to those of ordinary skill in the art upon a reading of the instant specification and a detailed consideration of applications for which specific apparatus is intended. Certain of these apparent modifications have been discussed hereinabove such as the latching of the timer relay 71 and the control relay means 72, the utilization of audible as well as visual indicia to indicate the various cycles of programmed operation, and the substitution of automatic timers exhibiting various characteristics.

Thus, while the invention has been described in connection with a specific exemplary embodiment thereof, it will be understood that many modifications will be readily apparent to those of ordinary skill in the art; and that this application is intended to cover any adaptations or variations thereof. Therefore, it is manifestly intended that this invention be only limited by the claims and the equivalents thereof.

What is claimed is:
1. Sterilizing apparatus comprising:
   a chamber for receiving objects to be subjected to elevated temperatures for predetermined intervals, said chamber including door means and means for sensing the opened and closed condition of said door means;
   heater means in fluid communication with said chamber;
   heater control means for selectively energizing said heater means, said heater control means exhibiting temperature sensitive characteristics and active, when enabled, to maintain the operation of said heater means in the vicinity of a predetermined temperature by the selective energizing and de-energizing thereof, said heater control means comprising first and second temperature controller means disposed in a primary and back-up relationship with respect to said heater means, each of said first and second temperature controller means controlling the application of operating potential to said heater means and being capable of selectively energizing or de-energizing said heater means;
   program initiation means for starting a cycle of operation of said sterilizing apparatus, said program initiation means including cycle controlling means, means for sensing the temperature within said chamber and means for momentarily applying potential to said cycle controlling means, said program initiation means being operatively connected to said heater control means and said door condi- tion sensing means and operative upon an enabling of said means for momentarily applying potential to said cycle controlling means to momentarily apply operating potential to said heater control means and said means for sensing the temperature within said chamber means, said cycle controlling means active upon a momentary application of operating potential thereto to continue an application of operating potential to said heater control means and said means for sensing the temperature within said chamber means if a closed door condition is sensed by said means for sensing the condition of said door means, said cycle controlling means being responsive to the disruption in a supply of operating potential to cause a resetting of said sterilizing apparatus whereupon a new cycle of programmed operation must be initiated;

automatic timer means for defining said predetermined intervals during which said objects are to be subjected to said elevated temperature, said automatic timer means being connected to said cycle controlling means and said means for sensing the temperature within said chamber, said automatic timer means being active to initiate a timing of said predetermined interval upon a detection of a selected temperature within said chamber by said means for sensing the temperature within said chamber and further active upon an expiration of a predetermined interval for de-energizing said cycle controlling means whereupon the application of operating potential to said heater control means and said means for sensing temperatures within said chamber is terminated.

2. The sterilizing apparatus according to claim 1 wherein said predetermined temperature maintained by said heater control means by the selective energizing and de-energizing of said heater means and said selected temperature detected within said chamber by said means for sensing temperature are similar in magnitude.

3. The sterilizing apparatus according to claim 1 wherein said program initiation means additionally includes means for locking said door means in a closed condition, said means for locking said door means in a closed condition being enabled when operating potential is applied to said cycle controlling means and disabled when operating potential is removed therefrom.

4. The sterilizing apparatus according to claim 1 wherein said means for sensing the temperature within said chamber comprises automatic temperature controller means having temperature sensor means disposed within said chamber.

5. The sterilizing apparatus according to claim 4 wherein said temperature sensor means comprises thermistor probe means disposed within said chamber.

6. The sterilizing apparatus according to claim 1 wherein said first temperature controller means is set to de-energize said heater means if a first temperature is exceeded and said second temperature controller means is set to de-energize said heater means if a second temperature is exceeded.

7. The sterilizing apparatus according to claim 6 additionally comprising:

first indicia means for indicating normal operation of said primary temperature controller means, said first indicia means being connected to said heater means and providing an indication whenever potential is being applied thereto; and second indicia means for indicating an operation of said back-up temperature controller means, said second indicia means being connected to said back-up temperature controller means and providing an advisory indication whenever said back-up temperature controller means has de-energized said heater means.

* * * * *